United States Patent
Deane et al.

(10) Patent No.: US 11,497,404 B2
(45) Date of Patent: Nov. 15, 2022

(54) METHOD AND SYSTEM FOR AUTOMATIC BRIGHTNESS/GAIN CONTROL WHILE MEASURING LOCALIZED ORAL INFLAMMATION

(71) Applicant: KONINKLIJKE PHILIPS N.V., Eindhoven (NL)

(72) Inventors: Steven Charles Deane, Cambridge (GB); Alan James Davie, Cambridge (GB); Vincent Jeanne, Migne Auxances (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 259 days.

(21) Appl. No.: 16/770,705

(22) PCT Filed: Nov. 22, 2018

(86) PCT No.: PCT/EP2018/082273
§ 371 (c)(1),
(2) Date: Jun. 8, 2020

(87) PCT Pub. No.: WO2019/115201
PCT Pub. Date: Jun. 20, 2019

(65) Prior Publication Data
US 2021/0161391 A1  Jun. 3, 2021

Related U.S. Application Data

(60) Provisional application No. 62/597,667, filed on Dec. 12, 2017.

(51) Int. Cl.
*A61B 5/00* (2006.01)
*G05B 11/01* (2006.01)
*A46B 15/00* (2006.01)

(52) U.S. Cl.
CPC .......... *A61B 5/0088* (2013.01); *A61B 5/4552* (2013.01); *G05B 11/01* (2013.01); *A46B 15/0034* (2013.01)

(58) Field of Classification Search
CPC ....... A61B 5/4552; A61B 5/00; A61B 5/0088; A61B 5/4547; A61B 5/7405; A61B 5/06;
(Continued)

(56) References Cited

U.S. PATENT DOCUMENTS

| 6,047,042 A | 4/2000 | Khutoryansky |
| 6,525,819 B1 | 2/2003 | Delawter |

(Continued)

FOREIGN PATENT DOCUMENTS

| CN | 101771824 A | * | 7/2010 |
| JP | 2009039475 A | * | 2/2009 |

(Continued)

OTHER PUBLICATIONS

International Search Report and Written Opinion, International Application No. PCT/EP2018/082273, dated Feb. 4, 2019.

*Primary Examiner* — Brenda C Bernardi

(57) ABSTRACT

A method (500) for localizing gingival inflammation using an oral care device (10), the method comprising: (i) emitting (520) light at a first intensity by a light emitter (42); (ii) obtaining (530) first reflectance measurements reflectance data; (iii) determining (540), by a controller (30) from the first reflectance data, whether the location comprises gingiva; (iv) automatically adjusting (550), based at least in part on the first reflectance data, the intensity of a light emitter to a second intensity different from the first intensity, and/or automatically adjusting (550) a gain of a light detector; (v) obtaining (560) a second plurality of reflectance measurements by the light detector of the oral care device for at least some of the locations; and (vi) determining (570), using the (Continued)

second plurality of reflectance measurements, whether gingiva at the location is inflamed.

15 Claims, 6 Drawing Sheets

(58) Field of Classification Search
CPC ....... A61B 5/065; A61B 5/7455; G05B 11/01; A46B 15/0034
See application file for complete search history.

(56) References Cited

U.S. PATENT DOCUMENTS

| | | |
|---|---|---|
| 7,916,282 B2 | 3/2011 | Duineveld |
| 9,101,329 B2 | 8/2015 | Ertl |
| 2002/0093563 A1 | 7/2002 | Cline |
| 2008/0026340 A1 | 1/2008 | Gerlach |
| 2010/0068673 A1 | 3/2010 | Yamada |
| 2013/0323673 A1 | 12/2013 | Hakomori |
| 2016/0270716 A1* | 9/2016 | Guan ................. A61B 1/24 |
| 2017/0280986 A1 | 10/2017 | Sekowski |
| 2020/0060550 A1* | 2/2020 | Pesach ............. A61B 1/0676 |

FOREIGN PATENT DOCUMENTS

| | | |
|---|---|---|
| WO | 2015069704 A1 | 5/2015 |
| WO | 2017125926 A1 | 7/2017 |

\* cited by examiner

METHOD AND SYSTEM FOR AUTOMATIC BRIGHTNESS/GAIN CONTROL WHILE MEASURING LOCALIZED ORAL INFLAMMATION

This application is the U.S. National Phase application under 35 U.S.C. § 371 of International Application No. PCT/EP2018/082273, filed on 22 Nov. 2018, which claims the benefit of U.S. Provisional Application No. 62/597,667, filed 12 Dec. 2017. These applications are hereby incorporated by reference herein.

FIELD OF THE INVENTION

The present disclosure is directed generally to methods and systems for improved detection of localized gingival inflammation using an oral care device via automatic brightness and/or gain control.

BACKGROUND

Proper tooth brushing, including length and coverage of brushing, helps promote long-term dental health. Many dental problems are experienced by individuals who either do not regularly brush their teeth or who do so inadequately, especially in a particular area or region of the oral cavity. Among individuals who do brush regularly, improper brushing habits can result in poor coverage of brushing and thus surfaces that are not adequately cleaned during a cleaning session, even when a standard brushing regimen, such as brushing for two minutes twice daily, is followed.

Indeed, it is estimated that 50% of the adult population in the United States is affected by periodontal disease, with severity of disease ranging from gingivitis to periodontitis. However, consumers are often not able to detect early signs of periodontal disease. Accordingly, such diseases may only be detected during dental visits when the disease is already advanced and significantly harder to treat.

Inflammation of tissues within the mouth is one of the key signs of periodontal disease. Detecting inflammation would signal the existence of a disease state, and would alert the individual to the need for treatment to address the issue. For example, inflammation of the gums can be reversible with proper home care if it is detected, while bone loss from periodontitis will require professional treatment. However, existing methods and devices are unable to adequately identify or quantify inflammation of tissues, particularly localized inflammation. For example, handheld devices with multiple detection probes detect very high levels of returned light from teeth versus lower levels of light returned from gingiva. Additionally, depending on the height of the probe over the gingiva, the returned light level can vary significantly. The dynamic range needed to measure these extremes complicates detector circuit design and may require high-resolution analog-to-digital converters (ADC) not normally present in affordable microcontrollers. Furthermore, the returned light level is different in different parts of the spectrum due to the absorption of the chromophores being sensed. When the apparent tissue oxygen saturation is calculated from the spectra, errors in the calculation will be dominated by the spectral component with the highest noise level.

Accordingly, there is a continued need in the art for oral care methods and devices that minimize noise while keeping the returned light signals for each region in an optimum dynamic range.

SUMMARY OF THE INVENTION

The present disclosure is directed to inventive methods and systems for detecting tissue inflammation using an oral care device. Various embodiments and implementations herein are directed to an oral care device configured to obtain measurements of gingival tissue to identify localized gingival inflammation. The oral care device comprises a sensor with a configuration of one or more light emitters and photodetectors or imagers to obtain information about gingival tissue at a plurality of sampled locations. The one or more light emitters are configured to emit light at a first intensity, and the photodetectors obtain reflectance measurements for a plurality of locations within the user's mouth. The device determines which of the locations comprise gingiva, and the device then automatically adjusts the intensity of the one or more light emitters illuminating the gingiva, and/or automatically adjusts the gain of the photodetectors corresponding to the gingiva. The one or more light emitters again emit light and the photodetectors obtain new reflectance measurements for the gingiva locations. The device then uses the new reflectance measurements to determine whether the gingiva at any of these locations is inflamed.

Generally in one aspect, a method for localizing gingival inflammation within a user's mouth using an oral care device is provided. The method includes: (i) emitting light at a first intensity by a light emitter of the oral care device; (ii) obtaining a first plurality of reflectance measurements by a light detector of the oral care device from a surface at each of a plurality of locations within the user's mouth to generate first reflectance data for each of the plurality of locations; (iii) determining, by a controller of the oral care device from the first reflectance data, for each of the plurality of locations, whether the surface comprises gingiva; (iv) automatically adjusting, based at least in part on the first reflectance data, the intensity of a light emitter corresponding to one of the plurality of surfaces to a second intensity different from the first intensity, and/or automatically adjusting a gain of a light detector corresponding to one of the plurality of surfaces; (v) obtaining a second plurality of reflectance measurements by the light detector of the oral care device for at least some of the plurality of locations; and (vi) determining, by the controller using the second plurality of reflectance measurements, whether gingiva at each of the plurality of surfaces determined to comprise gingiva is inflamed.

According to an embodiment, the intensity of the light emitter is adjusted such that the reflectance measurements are constrained with an optimum dynamic range of an analog-to-digital converter used to digitize the reflectance measurements.

According to an embodiment, the gain of the light detector is adjusted such that the reflectance measurements are constrained with an optimum dynamic range of an analog-to-digital converter used to digitize the reflectance measurements.

According to an embodiment, the automatically adjusting step comprises adjusting a gain of a light detector corresponding to a surface determined to comprise gingiva. According to an embodiment, the automatically adjusting step comprises adjusting a gain of a light detector corresponding to a surface determined not to comprise gingiva.

According to an embodiment, the automatically adjusting step comprises adjusting an intensity of a light emitter corresponding to a surface determined to comprise gingiva. According to an embodiment, the automatically adjusting step comprises adjusting an intensity of a light emitter corresponding to a surface determined to not comprise gingiva.

According to an embodiment, the method further includes the step of providing information regarding whether gingiva at a location comprises inflammation.

According to an aspect is a device configured to localize gingival inflammation. The device includes: a light emitter configured to emit light at a first intensity; a light detector configured to obtain first reflectance measurements from a surface at each of a plurality of locations within the user's mouth to generate first reflectance data for each of the plurality of locations in response to the light emitted at the first intensity, wherein the light detector is further configured to obtain second reflectance measurements from one or more of the surfaces to generate second reflectance data; and a controller configured to: (i) determine from the first reflectance data, for each of the plurality of locations, whether the surface comprises gingiva; (ii) automatically adjust, based at least in part on the first reflectance data, the intensity of a light emitter corresponding to one of the plurality of surfaces to a second intensity different from the first intensity, and/or automatically adjust a gain of a light detector corresponding to one of the plurality of surfaces; (iii) determine, from the second reflectance data obtained after said automatically adjusting step, whether gingiva at each of the plurality of surfaces determined to comprise gingiva is inflamed.

According to an embodiment, the controller is configured to adjust the intensity of the light emitter such that the second reflectance measurements are constrained with an optimum dynamic range of an analog-to-digital converter used to digitize the reflectance measurements.

According to an embodiment, the controller is configured to adjust the gain of the light detector such that the second reflectance measurements are constrained with an optimum dynamic range of an analog-to-digital converter used to digitize the reflectance measurements.

According to an embodiment, the controller is configured to automatically adjust a gain of a light detector corresponding to a surface determined to comprise gingiva. According to an embodiment, the controller is configured to automatically adjust a gain of a light detector corresponding to a surface determined not to comprise gingiva.

According to an embodiment, the controller is configured to automatically adjust an intensity of a light emitter corresponding to a surface determined to comprise gingiva. According to an embodiment, the controller is configured to automatically adjust an intensity of a light emitter corresponding to a surface determined to not comprise gingiva.

As used herein for purposes of the present disclosure, the term "controller" is used generally to describe various apparatus relating to the operation of an oral care apparatus, system, or method. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a method and device for detecting gingival inflammation using an oral care device. More generally, Applicant has recognized and appreciated that it would be beneficial to provide a system to detect localized tissue inflammation. Accordingly, the methods described or otherwise envisioned herein provide a device such as an oral care device configured to obtain measurements of gingival tissue. The oral care device comprises one or more of a variety of sensor arrays having one or more light emitters and light detectors to obtain information about gingival tissue at a plurality of sampled locations. The one or more light emitters are configured to emit light at a first intensity, and the photodetectors are configured to obtain reflectance measurements from locations within the user's mouth. The device determines which of the locations comprise gingiva, and the device then automatically adjusts the intensity of the one or more light emitters illuminating the gingiva, and/or automatically adjusts the gain one or more of the photodetectors corresponding to the location of the gingiva. The one or more light emitters again emit light and the photodetectors obtain new reflectance measurements for the locations determined to comprise gingiva. The device uses the new reflectance measurements to determine whether the gingiva at any of these locations is inflamed. The oral care device can report that information to the user or a third party.

The embodiments and implementations disclosed or otherwise envisioned herein can be utilized with any oral device, including but not limited to a toothbrush, a flossing device, an oral irrigator, or any other oral device. For example, one application of the embodiments and implementations herein is to assess inflammation of gingival tissues using a specialized handheld oral inflammation detection device. Another application is to assess inflammation of gingival tissues using an oral care device such as a toothbrush or flossing device. However, the disclosure is not limited to these specific applications and thus the disclosure and embodiments disclosed herein can encompass any oral device.

Figure 1:
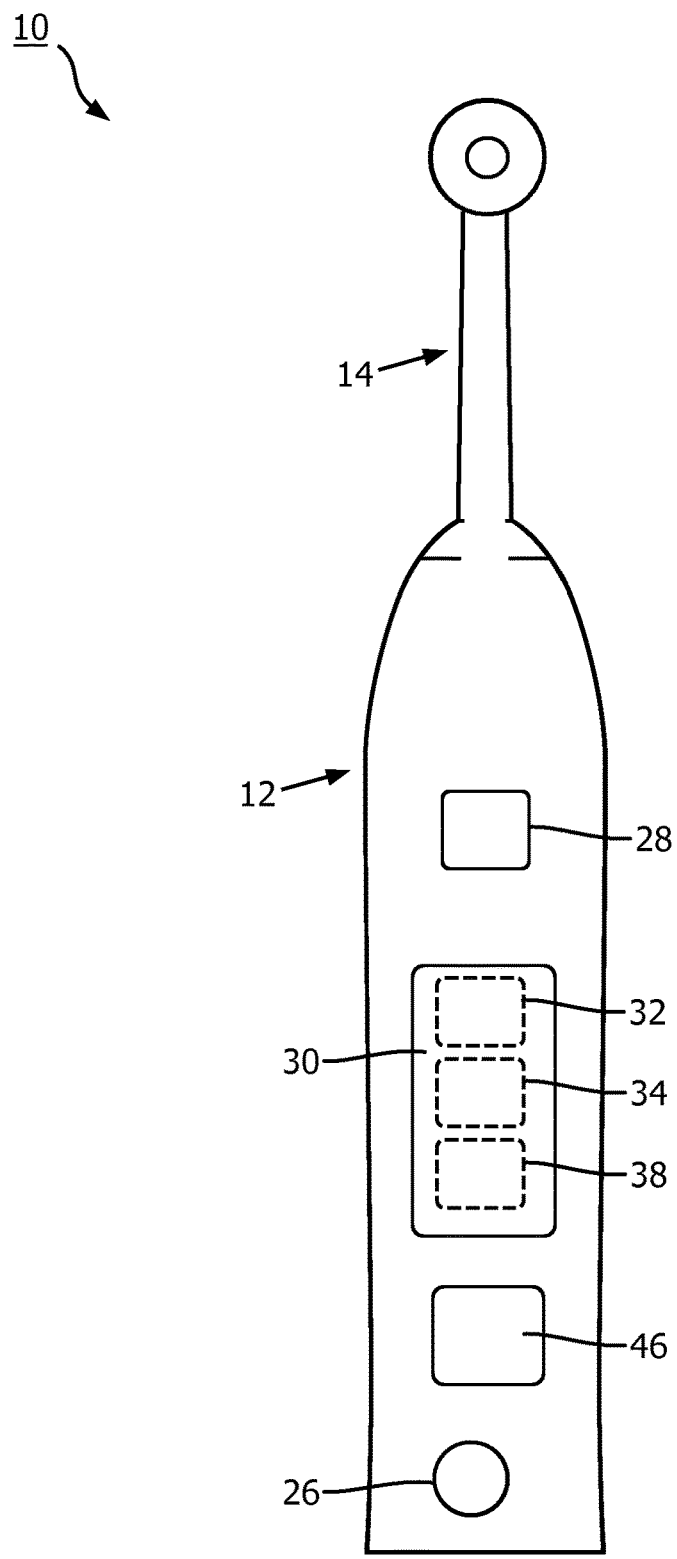
FIG. 1 is a schematic representation of an oral care device, in accordance with an embodiment.

Referring to FIG. 1, in one embodiment, is an oral care device 10 with a body portion 12 and a nozzle member 14 mounted on the body portion. According to an embodiment, nozzle member 14 is configured to allow the passage of pressurized liquid and/or air from a reservoir in the body 12 (not shown) to the nozzle where it is applied to the user's interdental regions. Nozzle member 14 can be detachably mounted onto body portion 12 such that the nozzle can periodically be replaced with a new one when a component of the device is worn out or otherwise requires replacement.

Body portion 12 is further provided with a user input 26. The user input 26 allows a user to operate the oral care device 10, for example to turn the oral care device on and off. The user input 26 may, for example, be a button, touch screen, or switch.

Oral care device 10 optionally includes one or more sensors 28. Sensor 28 is shown in FIG. 1 within body portion 12, but may be located anywhere within the device. Sensor 28 may be used to characterize the orientation and displacement of the device. According to an embodiment, these sensors provide information about the position of the device with respect to a user's body part, a fixed point, and/or one or more other positions. According to an embodiment, sensor 28 is disposed in a predefined position and orientation in the oral cleaning device 10, and the nozzle is in a fixed spatial relative arrangement to sensor 28. Therefore, the orientation and position of the nozzle can be easily determined based on the known orientation and position of the sensor 28.

The information generated by the sensor 28 is provided to a controller 30. Controller 30 may be formed of one or multiple modules, and is configured to operate the oral cleaning device 10 in response to an input, such as input obtained via user input 26. According to an embodiment, the sensor 28 is integral to the controller 30. Controller 30 can comprise, for example, at least a processor 32, a memory 34, and a connectivity module 38. The processor 32 may take any suitable form, including but not limited to a microcontroller, multiple microcontrollers, circuitry, a single processor, or plural processors. The memory 34 can take any suitable form, including a non-volatile memory and/or RAM. The non-volatile memory may include read only memory (ROM), a hard disk drive (HDD), or a solid state drive (SSD). The memory can store, among other things, an operating system. The RAM is used by the processor for the temporary storage of data. According to an embodiment, an operating system may contain code which, when executed by controller 30, controls operation of the hardware components of oral cleaning device 10. According to an embodiment, connectivity module 38 transmits collected sensor data, and can be any module, device, or means capable of transmitting a wired or wireless signal, including but not limited to a Wi-Fi, Bluetooth, near field communication, and/or cellular module.

According to an embodiment, oral care device 10 includes a user interface 46 configured to provide information to a user before, during, and/or after a care session. The user interface 46 can take many different forms, but is configured to provide information to a user. For example, the information can be read, viewed, heard, felt, and/or otherwise interpreted concerning inflammation of one or more tissues within the mouth. According to an embodiment, the user interface 46 provides feedback to the user that includes information about where tissues are inflamed, and/or how much inflammation is present. Accordingly, the user interface may be a display that provides information to the user, a haptic mechanism that provides haptic feedback to the user, a speaker to provide sounds or words to the user, or any of a variety of other user interface mechanisms. For example, the system may provide feedback via a smartphone app, a website, or via any other interface configured to share information with the user.

Figure 2:
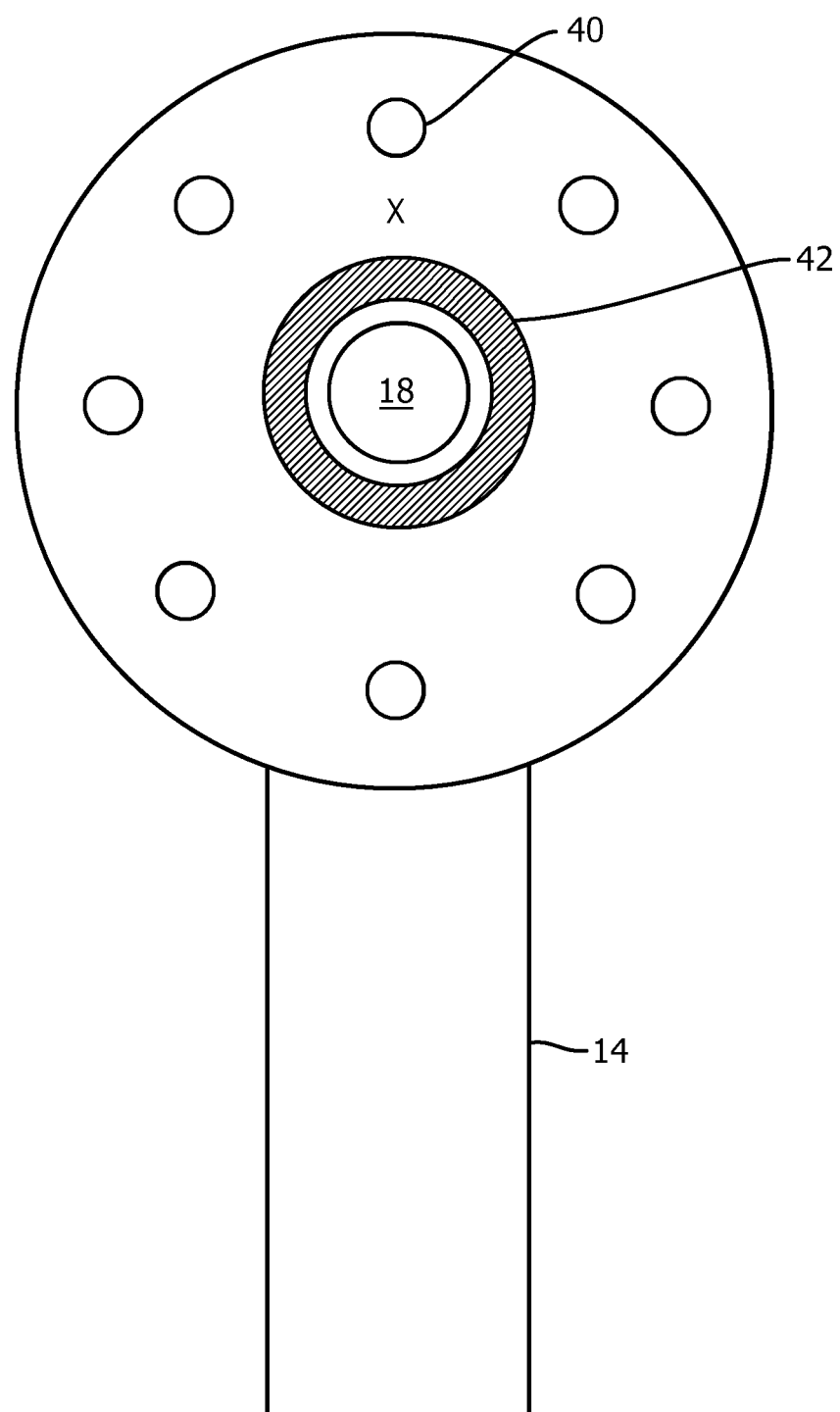
FIG. 2 is a schematic representation of a head of an oral care device, in accordance with an embodiment.

Referring to FIG. 2, in one embodiment, is a nozzle 14 of an oral care device. The nozzle includes a nozzle head portion, with a centrally-located guidance tip 18. According to one embodiment, the nozzle head comprises at least one light emitter 42 and at least one light receiver 40. According to the embodiment depicted in FIG. 2, the light emitter 42 is a ring-shaped bundle of light-emitting fibers or a light-emitting light guide, although it can be many other shapes and sizes. The one or more light emitters can be or comprise any light source, such as an LED light source, that emits light capable of facilitating the detection of gingival inflammation. According to an embodiment, the one or more light emitters comprise light from one or more light sources 48 such as LEDs, and are connected by a light fiber or light guide from the LEDs to the light emitter on the surface of the oral care device. According to an embodiment the light source generates light in at least two wavelengths, such as 480 nm and 680 nm that allows for the characterization of oxygen saturation in human tissue, and hence the detection of localized inflammation. Generally, tissue exhibiting low tissue oxygenation indicates gingival inflammation.

Similarly, the light receivers 40 are any light receivers capable of facilitating the detection of gingival inflammation. For example, according to an embodiment the light receivers are a photodetector or photodiode, or any other sensor capable of detecting light emitted by the light emitter 42. According to an embodiment, the light receivers are photodiodes connected to light fibers or light guides. Each light receiver may be configured to detect two or more wavelengths, or alternatively each light receiver may be configured to detect only a single wavelength. According to another embodiment, light receiver 40 is a pixel array configured to obtain one or more images of the tissue illuminated by the light emitted from the light emitter 42. The light receiver may comprise a plurality of detection fibers that are used simultaneously or may be time-multiplexed.

One advantage of the design of the oral care device in FIG. 2 is that the sensors are able to capture spatial information as well as gingival inflammation information. Since the information associated with each emitter-receiver couple comes from a unique tissue location, the localization of the inflammation is known.

In this embodiment, the guidance tip 18 provides a tactile feedback to the user, which facilitates proper interdental positioning near the gums. According to an embodiment, when properly positioned in the mouth, each light receiver 40 measures measures a different part of the tissue surface, which is approximately the location between the light emitter and the light receiver. For example, when placed on the junction between two teeth and the gingiva the light emitter will illuminate the whole area, and several light receivers 40 will be on the gingiva to detect inflammation, while others will be simultaneously placed on the teeth which can be easily distinguished from the measured spectral response.

Figure 3:
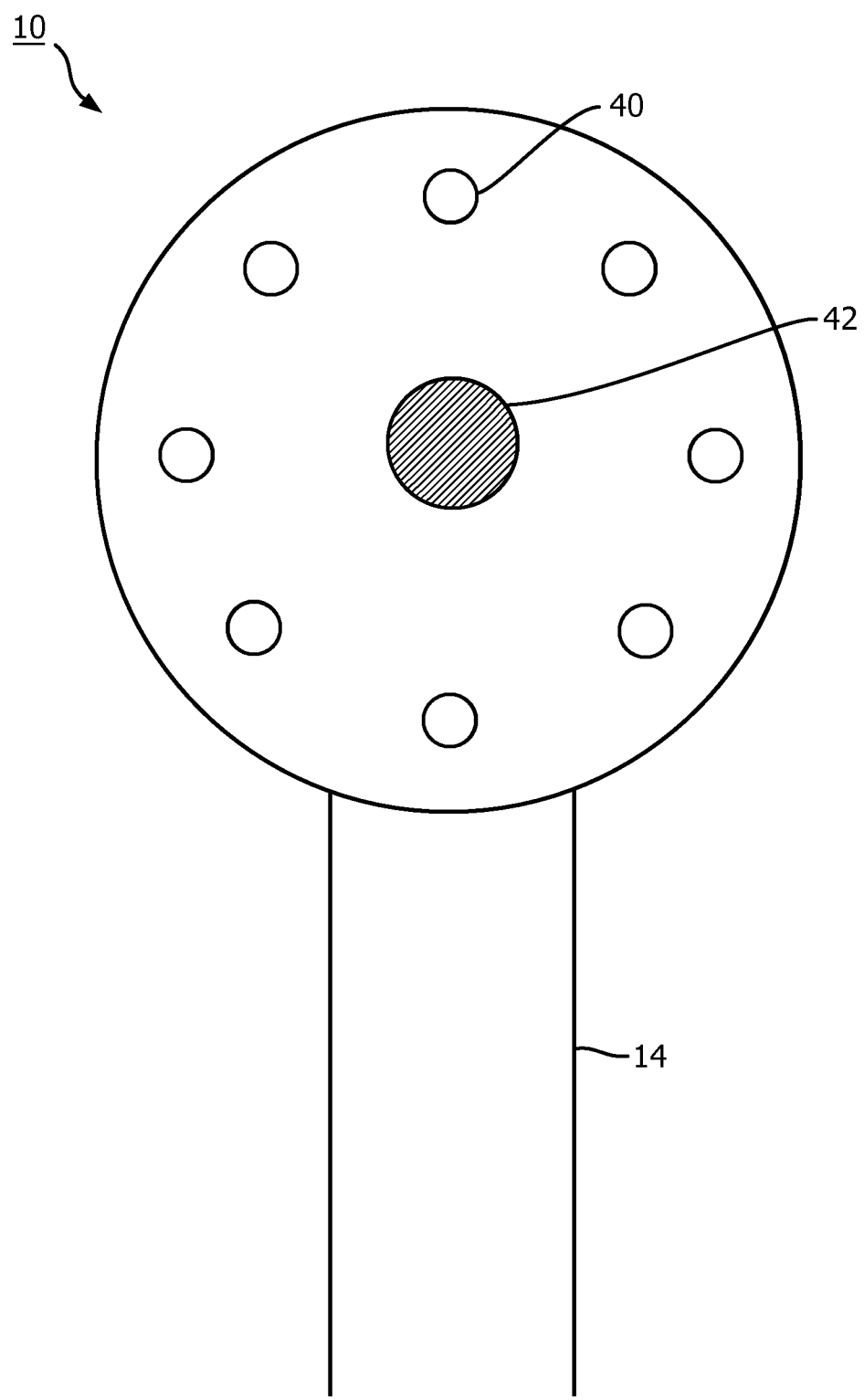
FIG. 3 is a schematic representation of a head of an oral care device, in accordance with an embodiment.

According to an embodiment, many different configurations of light emitters 42 and light detectors 40 are possible. Referring to FIG. 3, for example, is an embodiment of an oral care device 10 configured primarily to measure gingival inflammation. The oral care device comprises a head portion having a single centralized light emitter 42 and a plurality of light detectors 40. According to a similar embodiment, the device may comprise a single centralized light detector 40 and one or more light emitters 42.

The one or more light emitters 42 and light detectors 40 are positioned on device 10 such that the surfaces of the gingival tissue from which data is obtained are not directly illuminated by the light emitter. For example, referring to FIG. 2, the light emitter 42 emits light into the tissue in front of it, and light detector 40 obtains reflectance data from the tissue located at or very near the "X" shown on the device, although the light detector could also obtain reflectance data from the tissue located in front of it as well. According to an embodiment, therefore, the light emitters and the surfaces from which data is obtained are not overlapping. This is in contrast to a camera system in which imaged surfaces are directly illuminated. When a surface is directly illuminated, for example, detection or an image is dominated by near-surface scattering, which prevents the analysis of the gingival tissue as described herein.

Figure 4:
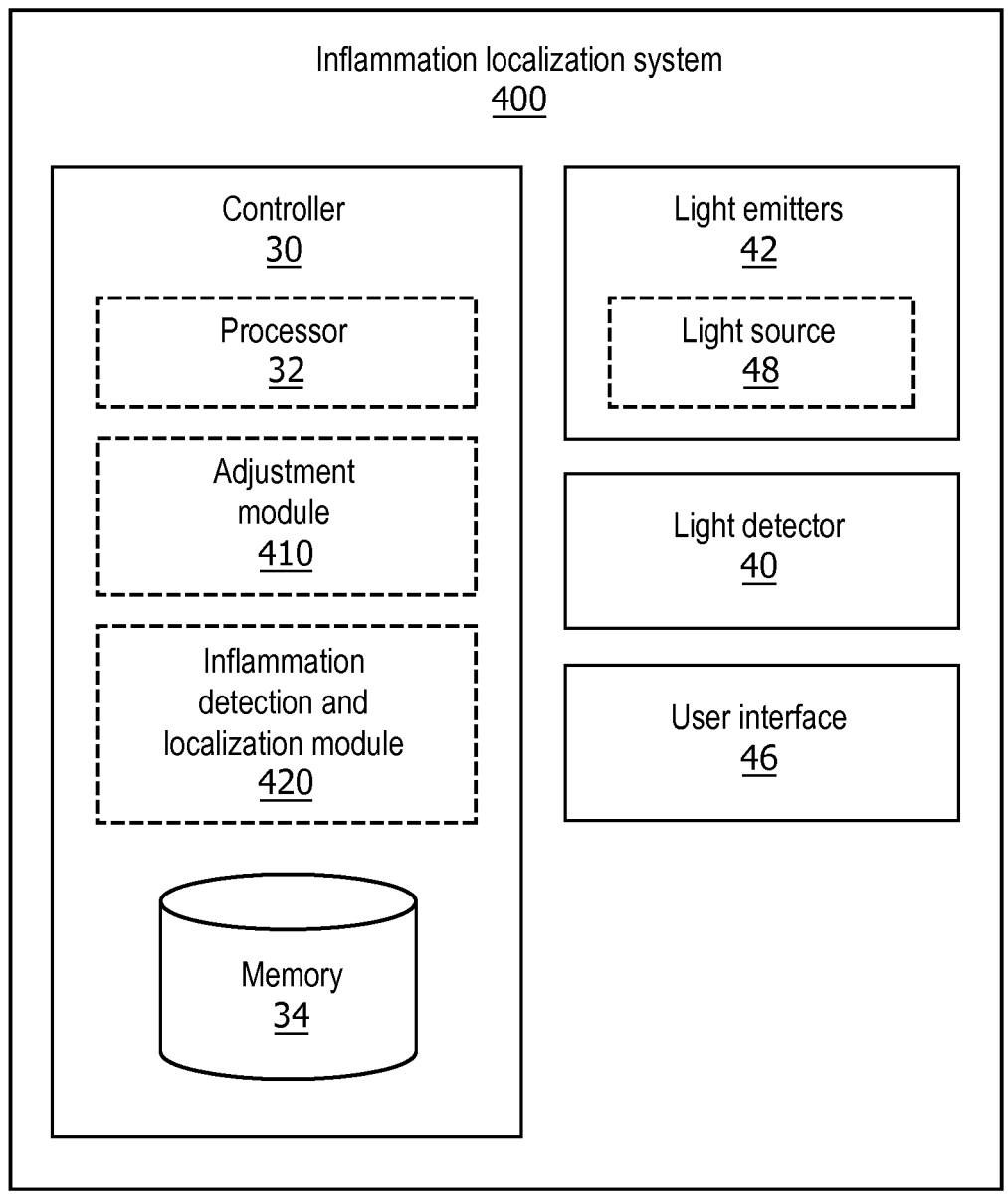
FIG. 4 is a schematic representation of an inflammation localization system, in accordance with an embodiment.

Referring to FIG. 4, in one embodiment, is an inflammation localization system 400. According to an embodiment, inflammation localization system 400 includes a controller 30 comprising a processor 32 and a memory 34. The inflammation localization system also comprises one or more light emitters 42 each with one or more light sources 48. Inflammation localization system 400 includes light detectors 40 which provide sensor data to the controller 30. Controller 30 of inflammation localization system 400 includes an adjustment module 410 which automatically adjusts an intensity of one or more of the light emitters 42, and/or automatically adjusts the gain of the light detectors 40. The adjustment module 410 may only adjust intensity, or may only adjust gain, or may do both.

Controller 30 of inflammation localization system 400 includes an inflammation detection and localization module 420. The inflammation detection and localization module analyzes reflectance data from the light detectors 40 to determine whether gingiva tissue is inflamed and where that tissue is located. The inflammation detection and localization module may also optionally include device localization information from sensor 28.

According to an embodiment, inflammation localization system 400 includes a user interface 46 which provides information to the user about the status and/or location of the tissue. User interface 46 can be or can comprise a feedback module that provides direct feedback to the user via a haptic signal, audio signal, visual signal, and/or any other type of signal.

According to an embodiment, inflammation localization system 400 can be implemented in any device configured to come into proximity with tissues that can be quantified. For example, inflammation localization system 400 can be implemented as an oral care device such as a toothbrush, an oral irrigator, a tongue cleaner, or any other oral care device.

Figure 5:
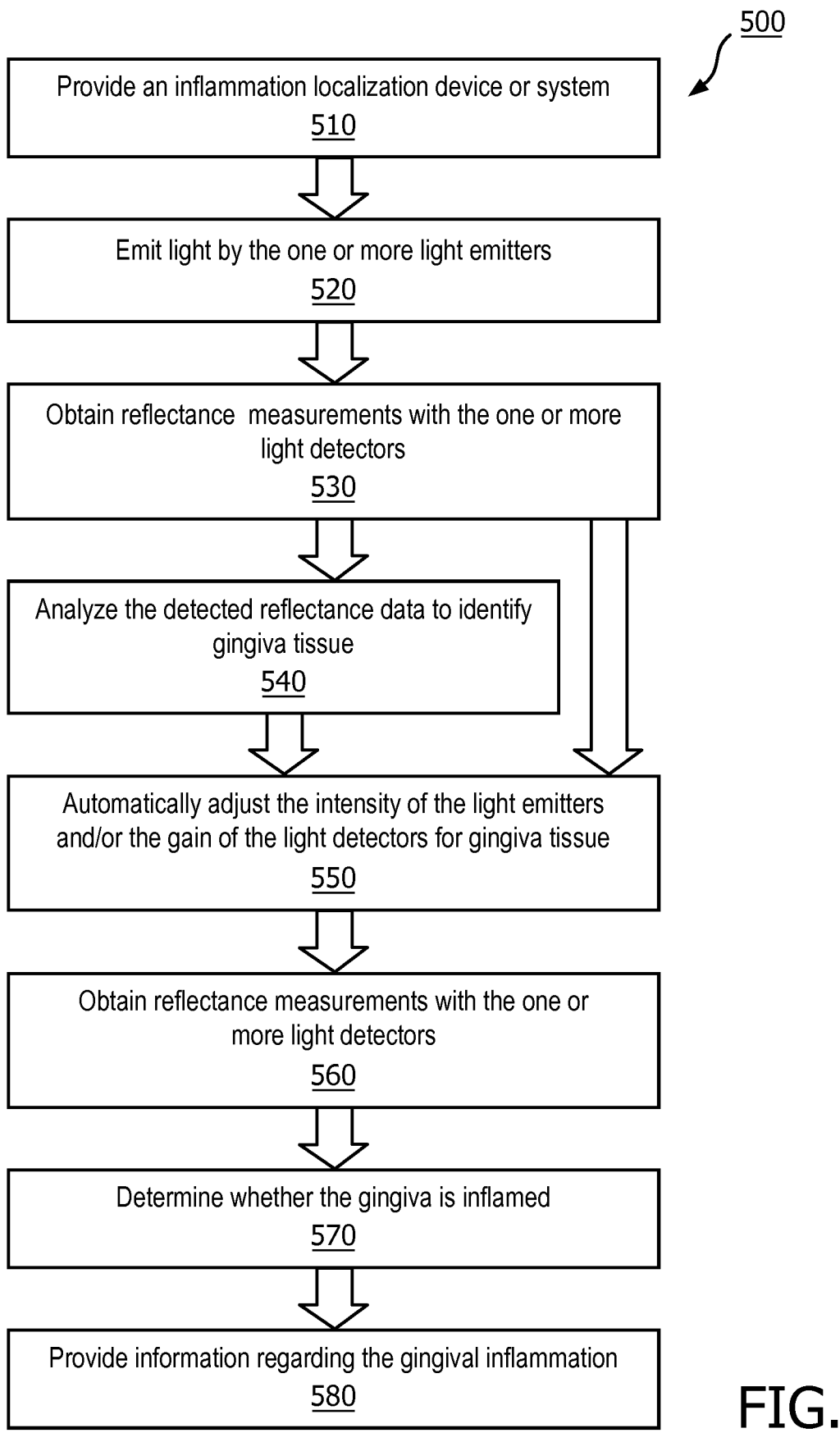
FIG. 5 is a flowchart of a method for localizing gingiva inflammation, in accordance with an embodiment.

Referring to FIG. 5, in one embodiment, is a flowchart of a method 500 for localizing inflammation of gingival tissue within a user's mouth. In step 510, an inflammation localization system 400 is provided. The inflammation localization system may be any of the devices or systems described or otherwise envisioned herein. Generally, the inflammation localization system will comprise one or more light emitters 42 with one or more light sources 48, light detectors 40, an adjustment module 410 configured to automatically adjust an intensity of one or more of the one or more light emitters 42 and/or automatically adjusts the gain of the one or more of the light detectors 40, and an inflammation detection and localization module 420 configured to analyze reflectance data to identify inflamed gingiva. Many other components and configurations are possible. Although method 500 is described within the framework of an oral care device 10, the method can be implemented using any other inflammation localization analysis system.

At step 520 of the method, one or more light emitters 42 emit light having a first intensity, a beam of each of which impacts the gingival tissue. According to an embodiment, the emitted light only indirectly impacts the gingival tissue that is analyzed by the light detector 40. A light emitter may comprise one or more light sources 48, and the system may be configured to activate the one or more light emitters in response to a trigger. The light emitters may be spaced apart or co-located, depending on the design of the device.

At least some of the one or more light emitters can be configured such that different wavelengths of light are emitted, and/or a light emitter can emit different wavelengths at different times. For example, the device may be configured such that different wavelengths are emitted by different light emitters, and/or the device may be configured such that different wavelengths are emitted by different light sources 48 of a light emitter 42. As a result, the device can comprise a plurality of emitted light wavelengths. According to an embodiment, for effective gingivitis detection, several wavelengths are sampled at each location to give a measured spectrum from which tissue oxygenation can be measured and gingival condition can be assessed. For example, high oxygenation indicates gum health while low oxygenation indicates gingivitis. The number of wavelengths can be as low as two, or it can be a detailed spectrum with hundreds of channels, although for most purposes the number of wavelengths is between four and eight.

At step 530 of the method, at least one light detector 40 obtains reflectance data, such as reflectance from the surfaces reflecting light emitted by the one or more light emitters 42, during the emission of light at step 520. The light detector may obtain data continuously or may only obtain data in response to a trigger. For example, the light detector may be triggered to obtain sensor data in response to activation of a light emitter.

As discussed herein, a light detector 40 may be positioned in a non-overlapping position relative to a light emitter 42 such that the detected tissue is only indirectly illuminated by the light from the light emitter. This configuration of the light detector(s) and the light emitter(s) results in a significant improvement in both the device and detection of inflammation. For example, the non-overlapping configuration described or otherwise envisioned herein maximizes the signal-to-noise ratio and enhances detection of localized gingival inflammation, among other benefits, by reducing near-surface scattering and other inhibitory factors. The light detectors 40 of the oral care device can be positioned in any position in or on the oral care device, and may be positioned to obtain information about a variety of locations of the mouth or other surface being analyzed.

According to an embodiment, the light detectors 40 are broadband detectors configured to obtain broadband spectral data. The light detectors will be configured to obtain, at a minimum, data for the wavelengths necessary to evaluate the oxygenation of the gingiva, to distinguish between gingiva and non-gingiva tissue, and/or other parameters necessary to perform care using the device. According to another embodiment, the light detectors 40 are narrowband detectors configured to obtain narrowband spectral data.

Once the light detectors 40 obtain reflectance data, that data can be communicated continuously or periodically to the controller. Optionally, the obtained reflectance data can be stored in a temporary or long-term memory for analysis at a later time.

At step 540 of the method, controller 30 of oral care device 10 analyzes the reflectance data to determine which of the plurality of analyzed locations are and/or are not gingiva. According to one embodiment, the inflammation detection and localization module 420, which can be implemented as an algorithm, analyzes the reflectance data in one or more steps. For example, as an initial step, the module rejects potential outliers in the data. Outliers may include spurious measurements, as well as reflectance data from objects that are likely not gingival tissues, such as food debris, teeth, and other objects. Since the absorption spectra of objects such as teeth and food debris vary considerably from the absorption spectra of gingival tissue, the two can be distinguished. According to an embodiment, outliers are detected at points with absorption spectra that do not correspond to gingival tissue, essentially not showing the sharp spectral characteristics of hemoglobin absorption.

According to an embodiment, inflammation detection and localization module 420 determines a reflectance ratio of two or more different wavelengths. Using sample data of spectra obtained at 550 nm and 660 nm, for example, a ratio of reflectance would provide values of 2.38 for gingival tissue and 1.21 for teeth. Similarly, a ratio of reflectance between a blue wavelength (400 nm to 480 nm) and a green wavelength (480 nm to 550 nm) would provide values of 5.96 for gingival tissue and 1.44 for teeth. Therefore, the inflammation detection and localization module 420 could be configured or programmed with predetermined thresholds to identify gingival tissue. According to an embodiment, the system compares the reflectance ratio to the predetermined threshold and characterizes the location as being gingiva or non-gingiva based on whether the determined reflectance ratio exceeds or does not exceed the predetermined threshold. As just one example, a threshold of 2 in both of the above examples would decipher between gingiva and non-gingiva; reflectance ratios above 2 are characterized as gingiva, and reflectance ratios below 2 are characterized as non-gingiva. The system would then discard data from non-gingiva and would only continue to analyze data obtained from gingiva.

According to another embodiment, at step 550 of the method the system analyzes the obtained reflectance data to determine which of the plurality of analyzed locations are and/or are not gingiva by weighting the reflectance data. For example, the system may apply a high weight to reflectance data indicative of gingiva, and/or may apply a low weight to reflectance data indicative of anything other than gingiva. A system configured to weight reflectance data may only apply a weight to reflectance data indicative of gingiva, may only apply a weight to reflectance data indicative of non-gingiva, or may apply weights to both conditions during an analysis. The weighting process may be a programmed or predetermined weighting process, or may be a machine-learned weighting process. Using a weighting process, the system may utilize the one or more weighting factors to focus on reflectance data indicative of gingiva for further analysis, including an analysis of possible inflammation. In addition to removing non-gingiva reflectance data, and weighting gingiva and/or non-gingiva reflectance data, other methods of determining which of the plurality of analyzed locations are gingiva are possible.

At step 550 of the method, the system automatically adjusts the intensity of the one or more light emitters corresponding to, or in proximity to, the location or locations determined to comprise gingiva tissue. Additionally or alternatively, the system automatically adjusts the gain of the light detectors corresponding to, or in proximity to, the location or locations determined to comprise gingiva tissue. According to one embodiment, the adjustment module 410, which can be implemented as an algorithm, analyzes the reflectance data and/or the determined locations of gingiva to adjust the intensity and/or gain.

According to one embodiment, the adjustment module 410 is configured to adjust the intensity and/or gain in order to keep reflectance signals for each location in an optimum dynamic range of the ADC used to digitize the samples while minimizing noise. For example, the intensity of the reflectance signals may be higher or lower for different parts of the spectrum due to the absorption of the chromophores being sensed. When tissue oxygen saturation is calculated from the reflectance signals, the errors in the calculation may be dominated by the spectral component with the highest noise level. According to an embodiment, the system can implement a feedback loop such as a control loop run in the microcontroller, or electronically implemented as feedback circuits in the system.

Figure 6:
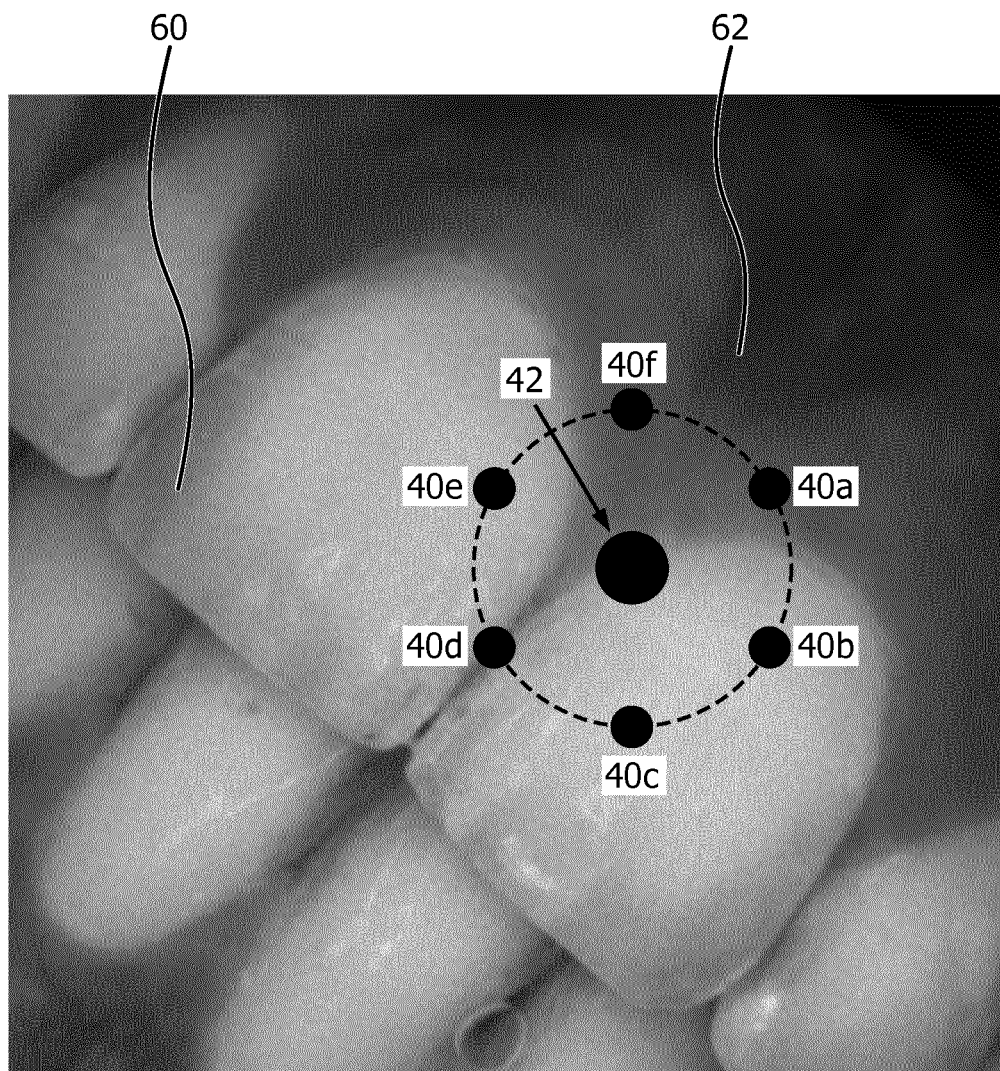
FIG. 6 is a schematic representation of a user's teeth and gingiva tissue, in accordance with an embodiment.

Referring to FIG. 6, in one embodiment, is a schematic representation of a user's teeth 60 and gingiva tissue 62. Aligned over the gingival and teeth tissues is an oral care device (not shown) with a plurality of light detectors 40*a-f* and a light emitter 42. FIG. 6 depicts an example of approximate locations where the light emitter will emit light into the tissue, and the light detectors will detect the emitted light. At step 530 of the method, each light detector 40*a-f* obtains reflectance measurements for the location corresponding to that light detector. Referring to FIG. 6, for example, light detectors 40*a* and 40*f* are located over gingiva, while the remaining light detectors are located over teeth. Accordingly, light detectors 40*a* and 40*f* located over gingiva will return much lower light levels than the remaining light detectors located over teeth which receive much higher light levels due to the increased reflectance.

Accordingly, the inflammation detection and localization module 420 may analyze the reflectance measurements to determine that light detectors 40*a* and 40*f* are located over gingiva, while the remaining light detectors are located over teeth. The adjustment module 410 can then analyze the reflectance data and/or the determined locations of gingiva to automatically adjust the intensity of the light emitter 42 and/or gain of the light detectors 40*a* and 40*f* in order to constrain the reflectance signals for each location in an optimum dynamic range of the ADC used to digitize the samples, and/or to minimize noise.

According to an embodiment, in a system where wavelength separation is performed at the source of light emissions, such as narrow band sources in a central illumination spot surrounded by a ring of wideband detectors for example, the gain for each region determined to comprise gingiva is automatically adjusted at the photodiode amplifier by the system. In this example, light detectors which are determined to be located over teeth (or are determined to not be located over gingiva) can be set to a low gain to avoid saturating the ADC. According to one embodiment, the ADC reading may be corrected by a known gain setting to give a correct overall reading for internal processing, although many other methods are possible. For example, the system may also or alternatively adjust the gain of light detectors which are determined to be located over gingiva.

According to an embodiment, in a system where wavelength separation is performed at the light detectors, such as wideband light sources in a ring surrounding a central detection spot for example, the gain for each region determined to comprise gingiva is automatically adjusted by, for example, modulating the illumination intensity of the light emitter to produce a similar signal amplitude at the detector circuits. Optionally, the microcontroller can correct the readings for the known illumination brightness differences if desired.

According to an embodiment, the gain or gains utilized by the system are selected by the adjustment module 410 only with regard to locations identified as comprising gingiva. This determination is based on previous readings, and classification of the spectra from each location as being gingiva or non-gingiva.

At 560 of the method, the one or more light emitters 42 of the oral care device 10 emit light, a beam of each of which impacts the gingival tissue. One or more of the light emitters 42 may be adjusted to emit light having a different intensity. For example, a light emitter may emit light having a different intensity, stronger or weaker, if that light emitter is determined to have obtained prior reflectance data from a location determined to be gingiva. As another example, all light emitters corresponding to a location other than gingiva may be automatically adjusted by the adjustment module 410 to emit light having a different intensity, stronger or weaker.

Similarly, the gain of one or more of the light detectors 40 may be automatically adjusted to constrain the reflectance signals for each location in an optimum dynamic range of the ADC used to digitize the samples, and/or to minimize noise. For example, the gain of a light detector may be adjusted, if that light detector is determined to have obtained prior reflectance data from a location determined to be gingiva. As another example, the gain of all light detectors corresponding to a location other gingiva may be automatically adjusted by the adjustment module 410.

At step 570 of the method, the controller 30 of oral care device 10 analyzes the new reflectance data obtained in step 560 to determine which of the analyzed locations comprise inflamed gingiva. For example, the inflammation detection and localization module 420 analyzes the new reflectance data for all locations or only at locations determined to comprise gingiva. This analysis can be done while the device is obtaining data, or may be completed after the oral care device has finished with a session, or it may be performed on demand from the user.

According to an embodiment, the inflammation detection and localization module 420 determines or characterizes an approximate tissue oxygenation level of the gingival tissue using the reflectance data. Since tissue oxygen saturation is significantly decreased in gingivitis and periodontitis locations compared to healthy locations, the module may select a signal exhibiting the lowest tissue oxygenation, which identifies the highest level of gingival inflammation. This may be performed, for example, by selecting the maximum value from a given set of data, or by taking the average of the X-top percentile from a given set of data, among other methods. The module may obtain this information, for example, at each locale for which data was obtained. The inflammation detection and localization module 420 will thus generate information about locations within the mouth where there is likely to be gingival inflammation.

At step 580 of the method, the system or device optionally provides feedback to the user and/or a third-party regarding the inflammation localization information. The user interface 46 of the oral care device 10, for example, can provide direct and/or indirect feedback to the user while the oral care device is being used, or after a cleaning or scanning session. As an example, the device can provide direct feedback to the user after each measurement using audio, visual, haptic, and/or digital feedback whenever inflammation is detected.

According to another embodiment, the system or device may provide feedback to the user after a scanning session is complete. As an example, the system or device may provide feedback once a scanning session is complete by means of visual representation where the inflammation levels are displayed. The feedback may include, for example, a mouth map—using location sensing technology during measurement—either in their absolute form to show the inflammation levels or in relative forms to highlight one or more specific sites. According to an embodiment, the device can scale or otherwise rank inflammation levels using a variety of colors or other physical representations. For example, the user may only focus on areas of significant inflammation, or inflammation above a certain level.

According to an embodiment, the inflammation data is stored and/or communicated with a third party, either locally or remotely. For example, according to an embodiment, a patient may be instructed to use the oral care device during an appointment with a dental care professional, to assess inflammation. The inflammation information will then be communicated to the dental care professional, using a report or other mechanism. As another example, a user may collect inflammation data that is automatically or periodically transmitted to a remote healthcare professional or other intended or authorized entity where it can be analyzed continuously or during an appointment with the user.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of" and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for localizing gingival inflammation using an oral care device having sensors capable of determining a position of the oral care device within the user's mouth the method comprising:
   providing feedback to the user based on the determined position of the device in the user's mouth to facilitate desired positioning of the device;
   when the oral care device is in the desired position, emitting light at a first intensity by a light emitter of the oral care device;
   obtaining a first plurality of reflectance measurements by a light detector of the oral care device from a surface at each of a plurality of locations within the user's mouth to generate first reflectance data for each of the plurality of locations;
   determining, by a controller of the oral care device from the first reflectance data, for each of the plurality of locations, whether the surface comprises gingiva;
   automatically adjusting, based at least in part on the first reflectance data, the intensity of a light emitter corresponding to one of the plurality of surfaces to a second intensity different from the first intensity, and/or automatically adjusting a gain of a light detector corresponding to one of the plurality of surfaces;
   obtaining a second plurality of reflectance measurements by the light detector of the oral care device for at least some of the plurality of locations; and
   determining, by the controller using the second plurality of reflectance measurements, whether gingiva at each of the plurality of surfaces determined to comprise gingiva is inflamed.

2. The method of claim 1, wherein intensity of light from the light emitter is adjusted such that the reflectance measurements are constrained with an optimum dynamic range of an analog-to-digital converter used to digitize the reflectance measurements.

3. The method of claim 1, wherein the gain of the light detector is adjusted such that the reflectance measurements are constrained with an optimum dynamic range of an analog-to-digital converter used to digitize the reflectance measurements.

4. The method of claim 1, wherein said automatically adjusting step comprises adjusting a gain of a light detector corresponding to a surface determined to comprise gingiva.

5. The method of claim 1, wherein said automatically adjusting step comprises adjusting a gain of a light detector corresponding to a surface determined not to comprise gingiva.

6. The method of claim 1, wherein said automatically adjusting step comprises adjusting an intensity of light from a light emitter corresponding to a surface determined to comprise gingiva.

7. The method of claim 1, wherein said automatically adjusting step comprises adjusting an intensity of light from a light emitter corresponding to a surface determined to not comprise gingiva.

8. The method of claim 1, further comprising the step of providing information regarding whether gingiva at a location comprises inflammation.

9. A device configured to localize gingival inflammation, comprising:
   a position sensor configured to sense the position of the device within a user's mouth;

a user interface configured to provide feedback to the user based on the sensed position of the device in the user's mouth to facilitate positioning of the device in a predetermined position, a light emitter configured to emit light at a first intensity and second intensity when the position of the device in the user's mouth is the predetermined position;

a light detector configured to obtain first reflectance measurements from a surface at each of a plurality of locations within the user's mouth to generate first reflectance data for each of the plurality of locations in response to the light emitted at the first intensity, wherein the light detector is further configured to obtain second reflectance measurements from one or more of the surfaces to generate second reflectance data; and a controller configured to: (I) determine from the first reflectance data, for each of the plurality of locations, whether the surface comprises gingiva; (ii) automatically adjust, based at least in part on the first reflectance data, the intensity of light from a light emitter corresponding to one of the plurality of surfaces to the second intensity different from the first intensity, and/or automatically adjust a gain of a light detector corresponding to one of the plurality of surfaces; (iii) determine, from the second reflectance data obtained after said automatically adjusting step, whether gingiva at each of the plurality of surfaces determined to comprise gingiva is inflamed.

10. The device of claim 9, wherein the controller is configured to adjust the intensity of the light from the light emitter such that the second reflectance measurements are constrained with an optimum dynamic range of an analog-to-digital converter used to digitize the reflectance measurements.

11. The device of claim 9, wherein the controller is configured to adjust the gain of the light detector such that the second reflectance measurements are constrained with an optimum dynamic range of an analog-to-digital converter used to digitize the reflectance measurements.

12. The device of claim 9, wherein the controller is configured to automatically adjust a gain of a light detector corresponding to a surface determined to comprise gingiva.

13. The device of claim 9, wherein the controller is configured to automatically adjust a gain of a light detector corresponding to a surface determined not to comprise gingiva.

14. The device of claim 9, wherein the controller is configured to automatically adjust an intensity of light from a light emitter corresponding to a surface determined to comprise gingiva.

15. The device of claim 9, wherein the controller is configured to automatically adjust an intensity of light from a light emitter corresponding to a surface determined to not comprise gingiva.

* * * * *